United States Patent [19]

Newman et al.

[11] Patent Number: 5,785,690
[45] Date of Patent: Jul. 28, 1998

[54] REFASTENABLE TUBE AND CABLE RESTRAINT FOR SURGICAL USE

[75] Inventors: Charles L. Newman, West Lakeland Township, Washington County, Minn.; Winfried Kipp, Borken, Germany

[73] Assignee: Minnesota Mining and Manufacturing Company, St. Paul, Minn.

[21] Appl. No.: 472,714

[22] Filed: Jun. 6, 1995

Related U.S. Application Data

[63] Continuation of Ser. No. 245,012, May 18, 1994, Pat. No. 5,463,231, which is a continuation-in-part of Ser. No. 208, 990, Mar. 10, 1994, abandoned.

[51] Int. Cl.⁶ ............................................. A61M 5/32
[52] U.S. Cl. .............................. 604/180; 128/DIG. 26
[58] Field of Search ........................... 609/174, 175, 609/179, 180; 128/DIG. 26

[56] References Cited

U.S. PATENT DOCUMENTS

| | | | |
|---|---|---|---|
| Re. 24,906 | 12/1960 | Ulrich | 206/59 |
| D. 256,162 | 7/1980 | Haerr et al. | D24/52 |
| 2,292,272 | 8/1942 | Hirshfield | 40/2 |
| 2,387,593 | 10/1945 | Lesser | 117/68.5 |
| 2,902,734 | 9/1959 | Walters | 24/7 |
| 3,430,300 | 3/1969 | Doan | 24/73 |
| 3,677,250 | 7/1972 | Thomas | 128/348 |
| 3,826,254 | 7/1974 | Mellor | 128/133 |
| 3,865,770 | 2/1975 | Blake | 260/27 R |
| 3,884,443 | 5/1975 | McMaster | 248/467 |
| 3,918,446 | 11/1975 | Buttaravoli | 128/133 |
| 3,926,185 | 12/1975 | Krzewinski | 128/132 D |
| 4,027,665 | 6/1977 | Scrivens | 128/132 D |
| 4,097,627 | 6/1978 | Nemeth et al. | 428/40 |
| 4,122,857 | 10/1978 | Haerr | 128/348 |
| 4,134,398 | 1/1979 | Scrivens | 128/132 D |
| 4,275,721 | 6/1981 | Olson | 128/133 |
| 4,324,236 | 4/1982 | Gordon et al. | 128/214 R |
| 4,324,237 | 4/1982 | Buttaravoli | 128/214 R |
| 4,333,468 | 6/1982 | Geist | 128/348 |
| 4,413,080 | 11/1983 | Blake | 524/187 |
| 4,457,754 | 7/1984 | Buttaravoli | 604/180 |
| 4,484,914 | 11/1984 | Brown | 128/DIG. 26 |
| 4,531,942 | 7/1985 | Turner | 604/180 |
| 4,534,762 | 8/1985 | Heyer | 604/180 |
| 4,569,960 | 2/1986 | Blake | 524/145 |
| 4,596,245 | 6/1986 | Morris | 128/132 D |
| 4,614,183 | 9/1986 | McCracken et al. | 128/132 R |
| 4,669,458 | 6/1987 | Abraham et al. | 128/133 |
| 4,678,462 | 7/1987 | Vaillancourt | 604/180 |
| 4,838,868 | 6/1989 | Forgar et al. | 604/180 |
| 5,010,899 | 4/1991 | Thompson | 128/849 |
| 5,019,071 | 5/1991 | Bany et al. | 604/389 |
| 5,037,397 | 8/1991 | Kalt et al. | 604/174 |
| 5,038,778 | 8/1991 | Lott | 128/207.17 |
| 5,098,399 | 3/1992 | Tollini | 604/180 |

(List continued on next page.)

FOREIGN PATENT DOCUMENTS

| | | |
|---|---|---|
| 1038716 | 9/1978 | Canada. |
| 0 145 142 | 6/1985 | European Pat. Off.. |
| 880632 | 10/1961 | United Kingdom. |
| 2 235 629 | 3/1991 | United Kingdom. |
| 2 251 796 | 7/1992 | United Kingdom. |

OTHER PUBLICATIONS

TNT Moborg International Ltd. product literature.

*Primary Examiner*—Michael A. Brown
*Attorney, Agent, or Firm*—F. Andrew Ubel

[57] ABSTRACT

The present invention provides a tube and cable restraint having: an attachment strip of flexible material having on its underside a coating of adhesive suitable for adhering to a surface; a holding strip of flexible material having a fixed end, a repositionable end and a bridging section between the fixed end and the repositionable end comprising a bridging strip; an adhesive layer between the bottom surface of said holding strip and the top surface of said attachment strip at least at each end of said restraint; and a finger tab. The present invention also provides surgical drapes and gowns with tube and cable restraints attached thereto.

19 Claims, 8 Drawing Sheets

U.S. PATENT DOCUMENTS

| | | | |
|---|---|---|---|
| 5,100,393 | 3/1992 | Johnson | 604/180 |
| 5,125,907 | 6/1992 | Philpott | 604/80 |
| 5,125,995 | 6/1992 | D'Haese et al. | 156/155 |
| 5,158,557 | 10/1992 | Noreen et al. | 604/389 |
| 5,160,315 | 11/1992 | Heinecke et al. | 602/57 |
| 5,219,336 | 6/1993 | Wilk | 604/180 |
| 5,221,265 | 6/1993 | List | 604/180 |
| 5,236,421 | 8/1993 | Becher | 604/180 |
| 5,266,401 | 11/1993 | Tollini | 428/343 |
| 5,270,111 | 12/1993 | D'Haese et al. | 428/356 |
| 5,304,146 | 4/1994 | Johnson et al. | 604/180 |

REFASTENABLE TUBE AND CABLE RESTRAINT FOR SURGICAL USE

This is a continuation of application Ser. No. 08/245,012, filed May 18, 1994, now U.S. Pat. No. 5,463,231 which is a continuation-in-part of U.S. patent application Ser. No. 08/208,990 filed Mar. 10, 1994 now abandoned.

FIELD OF THE INVENTION

This invention relates to tube and cable restraints used to temporarily fasten tubes and cables to a patient's body or to a surgical drape or gown. This invention also relates to surgical drapes and gowns having such restraints attached thereto.

BACKGROUND OF THE INVENTION

There is a great need to economically fasten or restrain elongated tubes or cables (hereinafter sometimes generically referred to as "tubes") to a patient's body or to a surgical drape or gown. For example, restraints are needed which can fasten feeding tubes or other cables to a patient, fasten irrigation and drainage tubes to a patient or to the patient's bed, or fasten other tubes and/or cables to a surgical drape, thus keeping the tubes and/or cables in an organized fashion and out of the way of the surgical field.

Depending on the type of tube or cable it is sometimes desirable that the tube or cable be easily adjusted through the restraint. By "adjusted" or "adjustable," is meant that the tube or cable should be able to slip through the restraint in response to a desired force. This allows the tube or cable to be adjusted easily should an additional length of tube or cable be needed on either side of the restraint. In other situations the adjustment of the tube or cable should be restricted and the tube or cable not allowed to easily slip through the restraint.

It is also desirable that the tube or cable be easily removed or released from the restraint without need to cut the tube or cable. Preferably, the tube or cable should be easily removed or released from the restraint without the restraint being damaged. More preferably, the tube or cable restraint should be refastenable. By "refastenable," is meant that the tube or cable restraint should allow multiple securings and releasings of the tubes and/or cables. This is in contrast to those restraints which only function to secure a cable once (i.e., the release of the cable causes destruction of either the securing means or the cable integrity). In addition, preferred tube and cable restraints should be easily used with only one hand. This allows the user to grasp one or more tubes and cables in one hand and still operate the restraint with the other hand. Most preferably, the tube or cable restraint should be easily used with one gloved hand.

Unfortunately, prior attempts to produce such a versatile tube and cable restraint have failed to achieve these requirements. The restraints are either too expensive, not adjustable, not refastenable, or lack ease of use and versatility. It would be desirable to produce a tube and cable restraint that is economical, refastenable, and versatile.

U.S. Pat. No. 5,266,401 (Tollini) discloses a securing tape comprising a base portion having a tab. The tab has a fixed end and a free end with the tab being formed by cutting it out of the tape. The free end of the tab is secured relative to the base portion using a hook and loop device.

U.S. Pat. No. 4,457,754 (Buttaravolli) discloses a multi-purpose securement strip for use on the body of a patient. The securement strip comprises a base strip of flexible material and an elongated flexible cover strip. The flexible cover strip is stated to be permanently affixed to the upper surface of the base strip using a nonreleasable adhesive layer or a mechanical means such as sewing.

RELATED APPLICATIONS

Of related interest are U.S. patent application Ser. Nos. 08/209,424; 08/208,990; and 08/245,012 which are herein incorporated by reference.

SUMMARY OF THE INVENTION

The present invention provides inexpensive tube and cable restraints which are both adjustable and refastenable. The restraints may be easily operated with only one hand and may be attached to a patient's skin or to a fabric surface such as a surgical drape or gown.

In general, the tube and cable restraints of the present invention comprise: an elongated attachment strip of flexible material having on its underside a coating of an adhesive for attachment to a surface; a holding strip of flexible material having a fixed-end, a repositionable end, and a bridging strip between said fixed end and said repositionable end; and (at least at each end of the restraint) an adhesive layer between the bottom surface of the holding strip and the top surface of the attachment strip. The tube and cable restraints further comprise a finger tab near the repositionable end to facilitate the partial peeling apart of the holding strip from the attachment strip. In a presently preferred embodiment the holding strip and adhesive layer (i.e., the "holding tape") are formed from a single sheet of an adhesive tape material. To prevent the separation of the holding tape from the attachment strip at the fixed end the holding tape is cut in a manner such that the "peel edge" is constrained at the hinge line. This may be accomplished, for example, by narrowing the width of the peeling layer. A portion of the holding tape is not peeled and remains firmly attached to the attachment strip (thus resisting further peeling past the hinge line). In a presently preferred embodiment both the attachment strip and the holding strip comprise plastic backed adhesive tapes.

BRIEF DESCRIPTION OF THE DRAWINGS

FIG. 1b illustrates a restraint constructed from two layers of single-sided adhesive tapes and FIG. 1c illustrates a restraint constructed from a layer of a double-sided adhesive tape and a layer of a non-adhesive film. The center portion of each restraint is not shown.

DETAILED DESCRIPTION OF THE INVENTION

Figure 1A:
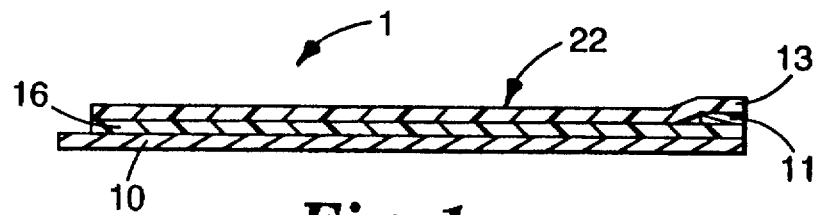
FIG. 1a is a cross section of a tube and cable restraint of the present invention having an attachment strip for securing the restraint to a surface and a holding strip for holding a tube or cable. The restraint is shown with a liner material which, prior to use, protects the exposed adhesive of the attachment strip.

The tube restraints of the present invention comprise: an elongated attachment strip of flexible material having on its underside a coating of an adhesive for attachment to a surface; a holding strip of flexible material having a fixed-end, a repositionable end, and a bridging strip; and (at least at each end of the restraint) an adhesive layer between the bottom surface of the holding strip and the top surface of the attachment strip. The tube and cable restraints further comprise a finger tab near the repositionable end to facilitate the partial peeling apart of the holding strip from the attachment strip. In a presently preferred embodiment the holding strip and adhesive layer are formed from a single sheet of an adhesive tape material. To prevent the separation of the holding tape from the attachment strip at the fixed end the holding tape is cut in a manner such that the "peel edge" is constrained at the hinge line. This may be accomplished, for example, by narrowing the width of the peeling layer. A portion of the holding tape is not peeled and remains firmly attached to the attachment strip (thus resisting further peeling at the hinge line). In a presently preferred embodiment both the attachment strip and the holding strip comprise plastic backed adhesive tapes.

The attachment strip provides a means for attaching the restraint to a surface (such as skin or a surgical drape, etc.) as well as providing a "landing zone" for attachment of the holding strip. Suitable attachment strips are readily attached to the desired surface and provide a new surface which is receptive to the holding strip and which provide the desired refastenability of the restraint. Thus, the attachment strip provides a linkage between the holding strip and the surface being secured to. In a presently preferred embodiment, the attachment strip further comprises a removal tab, as illustrated herein, to facilitate removal of the restraint from the surface after use. This feature is particularly advantageous when the restraint is utilized with a reusable article such as a surgical drape. The removal tab is preferably at the end of the restraint away from the repositionable end (i.e., preferably away from the finger tab and near the fixed end).

In one embodiment, the attachment strip comprises a "single-sided" adhesive tape (i.e., a tape comprising a backing and a pressure sensitive adhesive "PSA" coated on one side of the backing) preferably covered prior to use with a liner material. The liner material may be easily peeled away from the tape to expose the adhesive leaving the single-sided adhesive tape free for attachment to the surface. The non-adhesive side of the single-sided adhesive tape provides a compatible surface for repositionably adhering the holding strip. Preferably, the non-adhesive side of the single-sided adhesive tape is coated with a low adhesive backsize ("LAB") to facilitate easy peel release of the holding strip. Suitable single-sided adhesive tapes are discussed below. In another embodiment, the attachment strip comprises a "double-sided" adhesive tape (i.e., a tape comprising a backing and a PSA coated on both sides of the backing). A first side of the double-sided adhesive tape is preferably covered, prior to use, with a liner material. The liner material may be easily peeled away from the tape to expose one of the adhesive surfaces leaving the double-sided adhesive tape free for attachment to the surface. The other side of the double-sided adhesive tape is covered with the holding strip. Suitable double-sided adhesive tapes are discussed below.

A holding strip lies atop the attachment strip and, in use, covers the tube or cable being secured. Preferably, the holding strip is constructed from a single sheet of material. The holding strip is attached to the attachment strip at least two ends. One end of the holding strip (i.e., the "fixed-end") is permanently attached to the attachment strip. By "permanently" attached is meant that in use the holding strip and attachment strip do not separate at the fixed-end. The other end of the holding strip (i.e., the "repositionable end") is repositionably attached to the attachment strip. By "repositionably" attached is meant that the holding strip and attachment strip are separated during use and reconnected to secure a cable or tube. The center portion of the holding strip is termed the "bridging strip." The center portion of the restraint is termed the "bridging section." As discussed below the bridging section may be free of adhesive. For ease of manufacturing, however, the bridging section will often contain the same adhesive as is used to secure the fixed-end and/or the repositionable end to the attachment strip.

The holding strip is preferably cut, as herein described, to create integral "peel stops." The peel stops prevent the total peeling apart of the holding strip from the underlying attachment strip at the fixed end. Thus the user can easily peel the holding strip apart from the underlying attachment strip up to a "hinge line." At the hinge line the peeling is arrested. The integral peel stops provide important advantages over other mechanical or adhesive methods which might be employed to try to prevent undesirable separation at the fixed-end. First, the restraints of the present invention are of essentially one uniform thickness at the fixed end. There is no bulge due to a mechanical staple or sewing. Second, the restraints of the present invention when attached to fabrics can be easily folded and bent without damage. Furthermore, there is no need to coat the holding means with more than one type of adhesive (i.e., the same adhesive can be utilized for both the fixed-end and the repositionable end).

The holding strip should be flexible enough to easily peel back on itself and bend to form a bridge over a cable. Materials which easily break or tear when so folded or bent are considered to be unsuitable for use in this invention. The attachment strip and bridging strip's flexibility should be maintained over the entire operating range of the restraint. Materials which lose their flexibility either at extremely low temperatures (e.g., at 0° C.) or at extremely high temperatures (e.g., at 100° C.) should be avoided.

The attachment strip and holding strip should be sufficiently strong, for a given width, to support the forces which may be imparted upon it from the cable. Preferably, the strips should be sufficiently strong to support the gravitational weight of the cable, more preferably, the strips should be sufficiently strong to resist moderate "tugging forces" which may be imparted to the restraint when the covered cable is pulled or jerked. Most preferably, the bridging strip has a sufficient strength to resist tearing or breaking prior to the adhesive failure between the surface and the attachment strip, the adhesive failure between the holding strip and the attachment strip, the breaking of the cable being secured, or the cohesive failure of the surface being attached to (such as a tearing of a drape material). Suitable attachment and bridging strip materials have a tensile strength of at least 4 N/cm width when tested according to ASTM D882 as herein modified. Preferred attachment and bridging strip materials have a tensile strength of at least 5 N/cm width, more preferably at least 10 N/cm width, most preferably at least 13 N/cm width. If desired, the attachment strip or bridging strip material may comprise a layer of a toughening material (e.g., a layer of glass fibers oriented in the lengthwise direction or a layer of another high strength sheet material) to strengthen the strip.

Suitable attachment and holding strip materials for use in the present invention include sheet materials or laminates comprising cloth, nonwoven fabrics, foams or plastic materials. Presently preferred attachment and holding strip materials include plastic sheet materials. Suitable plastic sheet materials include naturally based organic polymers such as acetate, azlon, rayon, and triacetate; and synthetically prepared organic polymers such as acrylic, aramid, nylon, olefin (e.g., poly(1-butene), polycarbonate, polyethylene, polyester, poly(3-methyl-1-butene), poly(1-pentene), polypropylene, and polystyrene), polysulfone, polytetrafluoroethylene, poly(vinyl alcohol), poly(vinyl chloride), poly(vinylidine chloride), and poly(vinylidine fluoride). Preferred synthetic polymers include; acetate, acrylic, nylon, polypropylene, polyethylene, polyester, and rayon. Most preferred synthetic polymers include polyester and polyethylene films. Preferred materials are nontoxic, more preferably hypoallergenic, and are most preferably also environmentally safe (e.g., may be recycled or disposed of in a manner which does not harm the ecosystem).

If desired, the attachment or holding strip material may comprise an elastomeric material. Suitable elastomeric materials include natural rubber, polyisoprene, polybutadiene, diene styrene copolymers, ethylene propylene copolymers, ethylene propylene diene terpolymers, styrene butadiene block copolymers, styrene isoprene block copolymers, and polyurethanes such as spandex.

As previously mentioned, the attachment or holding strip material may comprise a laminate of more than one material. For example, a first material may be bonded, coated, or secured to a different second material. The first material may provide the laminate with the necessary compatibility with the adhesive layer (as discussed below) while the second material may provide the laminate with the necessary physical integrity or strength.

The holding strip material should be compatible with the adhesive used to secure it to the attachment strip. The attachment strip material should be compatible with the adhesive used to secure it to the surface and to the holding strip.

When formed into a bridge the bridging strip material and attachment strip material surrounds the tube or cable. Depending on the type of tube or cable it is sometimes desirable that the tube or cable be easily adjusted through the restraint. By "adjusted," is meant that the tube or cable should be able to slip through the restraint in response to a desired tension force. This allows the tube or cable to be adjusted easily, even without opening the bridge, should an additional length of tube or cable be needed on either side of the restraint. In other situations the adjustment of the tube or cable should be restricted and the tube or cable not allowed to easily slip through the restraint. The ability of a given tube to slip through a bridge of a particular restraint depends on the friction (or adhesion) between the bridging strip and attachment strip materials and the tube. Notably, the presence of an adhesive layer in the region of the bridge can affect the slip. To prevent or limit slip of the tube through the bridge one would preferably coat the bridging strip (or the attachment strip in the region of the bridge) with an adhesive. In contrast, to allow easy repositionability through a bridge one would select materials having a low friction coefficient with the tube.

The holding strip should be long enough to both bridge the tube(s) or cable(s) being secured and repositionably attach to the attachment strip. In a preferred embodiment an elongated strip of flexible material is used to form the bridging strip as well as provide areas for the placement of the adhesive used to permanently fix one end of the holding strip to the attachment strip and repositionably fix the other end. Thus, the holding strip material should be long enough to provide: a suitably sized bridge over the desired tube(s) or cable(s); a suitable region for placement of adhesive at each end; and, preferably, a suitably sized finger tab. Preferred tube and cable restraints for use in the medical field comprise a bridging strip of at least 5 cm, more preferably at least 8 cm, and most preferably at least 10 cm. To accommodate the fixed end, repositionable end, and finger tab, preferred tube and cable restraints comprise an elongated strip of flexible material of at least 9 cm, more preferably at least 12 cm, and most preferably at least 14 cm. Longer restraints may be utilized if desired.

The width of the restraint will depend on several factors. For example, the minimum strength requirements to function as a restraint may determine a minimum width and/or thickness for a particular holding strip material. In addition, the minimum required surface area of the attachment strip and/or fixed end or repositionable end of the holding strip may dictate a minimum width of the restraint. Furthermore, it is contemplated that the dimensions (e.g., width) required for the holding strip may not be the same as the dimensions required for the attachment strip. For example, a wider attachment strip may be utilized with a narrower holding strip. However, for reasons of economy, it is presently preferred to fabricate the restraints of the present invention in a generally rectangular shape. Thus, the width of the holding strip and attachment strip are preferably similar. Preferred tube and cable restraints for use in the medical field have an overall width of at least 1 cm, more preferably at least 2 cm, and most preferably between 2 and 5 cm.

The thickness of the bridging strip of the present invention should be sufficient to provide the bridge with enough strength. The minimum thickness will generally depend on the width of the bridging strip (in general, the strength of a material depends on the material's "cross section"). Suitable films used to form typical restraints of the present invention (for either the attachment strip or holding strip) have a thickness of at least 0.02 mm, more preferably a thickness of at least 0.04 mm, and most preferably a thickness between 0.07 and 0.2 mm.

The restraints of the present invention may be pre-attached to an article (such as a surgical drape or gown) or may be provided as individual restraints which are attached to a surgical drape or gown at the time of use. In addition, the restraints of the present invention may be provided as individual tube and cable restraints which are attached to a patient's skin at the time of use. Depending on the intended use the adhesive layer of the attachment strip may be covered with a liner material.

For use with pre-attached restraints on an article the attachment strip comprises a suitable adhesive attachment means. Suitable adhesive attachment means include, for example, thermoplastic or thermosetting adhesives, pressure sensitive adhesives ("PSA") or tapes comprising the same. Preferred adhesive attachment means include the pressure sensitive adhesives or PSA tapes discussed herein. Preferably, the attachment means is "permanent," i.e., the restraint, once attached to the drape or gown, is not relocatable on the drape or gown and is permanently attached to that position.

For use with individual "point-of-use" restraints (i.e., restraints which are individually provided for attachment to a drape, gown or a patient's skin at the time of use) the attachment means is preferably an adhesive attachment means covered prior to use with a liner. The adhesive attachment means is preferably coated on the surface of the elongated strip of flexible material. The adhesive attachment means may comprise one or more adhesive layers and optionally one or more backing layers. To protect the adhesive attachment means from surface contamination, the adhesive surface is preferably covered (e.g., with a separate liner material) prior to use. If desired, the adhesive surface may be covered prior to use with another portion of the elongated strip, or another restraint (i.e., a stack of restraints) instead of a separate liner material.

Suitable pressure sensitive adhesives for use in the present invention include those pressure sensitive adhesives which are capable of providing the necessary amount of peel strength and/or shear strength to function in the manner required. For example, suitable pressure sensitive adhesives have sufficient strength, when used as the attachment means, to securely attach the restraint to the surface without unintended detachment. In addition, suitable pressure sensitive adhesives have sufficient shear strength to securely attach the holding strip to, the attachment strip to prevent undesired opening of the bridge, yet have a peel strength that allows easy opening of the bridge by the user. Suitable adhesives for use in the medical field should be non-toxic, preferably hypoallergenic, and are most preferably also environmentally safe.

Suitable pressure sensitive acrylate adhesives for use in the present invention include copolymers which are reaction products of the polymerization of at least one "A" monomer and at least one "B" monomer to yield a copolymer having an inherent viscosity of about 1.0 dl/g to about 2.0 dl/g. The A monomer is a polymerizable monomer comprising an acrylate or methacrylate ester of a non-tertiary alcohol or a mixture of non-tertiary alcohols with the alcohols having from 1 to 14 carbon atoms and desirably averaging about 4 to 12 carbon atoms. The B monomer is an ethylenically unsaturated compound and desirably may be acrylic acid, methacrylic acid, itaconic acid, acrylamide, methacrylamide, acrylonitrile, methacrylonitrile, vinyl acetate, N-vinyl pyrrolidone, or combinations thereof. The A monomer is polymerizable and contributes the viscoelastic properties of the pressure sensitive adhesive copolymer. Non-limiting examples of such A monomers include the esters of acrylic acid or methacrylic acid with non-tertiary alkyl alcohol such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like. Such monomeric acrylic or methacrylic esters are known in the art, and many are commercially available. The B monomer is an ethylenically unsaturated compound copolymerized with the A monomer to affect the physical properties of the resulting pressure sensitive adhesive copolymer. In general, the presence of the B monomer will reduce the flexibility of the resulting pressure sensitive adhesive copolymer. Thus, the weight percentages of the A monomer and the B monomer should be balanced in order to provide a pressure sensitive adhesive copolymer having an inherent viscosity of from about 1.0 dl/g to about 2.0 dl/g. The weight percentage ratio of A monomer: B monomer ranges from about 85:15 to about 98:2 and desirably from about 90:10 to 97:3.

The pressure sensitive adhesive copolymer should be tacky at room temperature as well as at skin temperature of mammals. Also, the adhesive should be hypoallergenic, i.e., after continuous contact with skin, there is no significant skin sensitization or irritation during adhesion. Often, to determine if an adhesive is hypoallergenic, the following evaluations are conducted: cell cytotoxicity, skin irritation, and sensitization potential. The United States Food and Drug Administration recommends such evaluations in a Tripartite Biocompatibility Draft Guidance for Medical Devices. The commercially available medical tapes described herein using acrylate pressure sensitive adhesives of the type described herein are generally considered hypoallergenic. Presently preferred as an acrylate pressure sensitive adhesive for tapes used in the present invention is an isooctyl acrylate/acrylic acid copolymer in a weight ratio of about 94:6. The inherent viscosity of the copolymer is about 1.4–1.6 dl/g. Preferably, acrylate pressure sensitive adhesives have a tackifier added to the formulation to improve tack. Commercially available tackifiers include "Foral" branded colophony acid rosins, such as "Foral AX" and "Foral 85" rosins, commercially available from Hercules Corporation, and partially hydrogenated methylstyrene hydrocarbon resins, such as "Piccolastic A25" resin, also commercially available from Hercules Corporation. Such tackifiers can be added during preparation of the acrylate pressure sensitive adhesive in an amount of about 35–40 weight percent of the copolymer solids.

Alternate pressure sensitive adhesives useful in the present invention are hypoallergenic Kraton rubber-based pressure sensitive adhesives produced using styrene-butadiene or styrene-isoprene copolymers commercially available as Kraton branded copolymers from Shell Oil Company of Houston, Tex. A variety of Kraton based pressure sensitive adhesives are disclosed in U.S. Pat. Nos. 5,019,071 (Bany et al.) and 5,158,557 (Noreen et al.), the disclosures of which are incorporated by reference herein. Preferred as Kraton rubber-based pressure sensitive adhesives are Kraton 1107, Kraton 1111, Kraton 1101, and Kraton D branded copolymers, tackified with compatible tackifiers such as Escorez™ 1310LC branded tackifier commercially available from Exxon Chemicals, a solid $C_5$ tackifying resin commercially available as Wingtack™ Plus brand tackifier from Goodyear Tire and Rubber Company, Akron, Ohio and naphthenic oils having 10% aromatics commercially available as Shellflex™ 371 from Shell Oil Company. Such tackifiers can comprise about 45 to about 70 weight percent of the pressure sensitive adhesive, while the Kraton copolymer can comprise about 30 to 55 weight percent. Presently preferred is a Kraton based pressure sensitive adhesive comprising about 35 weight percent Kraton 1111, about 53 weight percent Wingtack Plus, about 11 weight percent Shellflex 371, and about 2 weight percent Irganox 1010 and 1076 branded antioxidants, in a similar formulation to that disclosed in Examples 1–13 of U.S. Pat. No. 5,019,071.

Additional alternate pressure sensitive adhesives useful in the present invention are the water-dispersible pressure sensitive adhesives disclosed in U.S. Pat. Nos. 3,865,770; 4,413,080; 4,569,960; 5,125,995; and 5,270,111 and in U.S. patent application Ser. Nos. 07/763,823; 07/889,647; and 08/093,080 the disclosures of which are herein incorporated by reference.

Pressure sensitive adhesive copolymers can be copolymerized using known polymerization techniques such as emulsion polymerization and solution polymerization. Sources of polymerization preparation and techniques include *Organic Polymer Chemistry*, Saunders et al. (Halsted Publishing Company, New York 1973); *Applied Polymer Science*, Tess et al. (American Chemical Society, Washington, D.C., 1981); *Principles of Polymerization*, Odien (John Wiley and Sons, New York, 1981); and the *Handbook of Pressure-Sensitive Adhesive Technology, Second Edition*, Satas, Ed., (Van Nostrand Reinhold Company, New York, 1989), the disclosures of which are incorporated by reference. Specifically, acrylate pressure sensitive adhesive copolymers can be prepared according to U.S. Pat. No. 2,884,126/RE 24,906 (Ulrich), the disclosure of which is incorporated by reference herein. The presently preferred acrylate copolymer pressure sensitive adhesive can be prepared by emulsion polymerization according to Example 5 of U.S. Pat. No. 2,884,126/RE 24,906, except that tackifier is added to the emulsion in an amount of about 35–40% weight percent of copolymer solids, and that tackified copolymer is dissolved in a heptane-isopropanol (70:30) solution. The presently preferred Kraton copolymer pressure sensitive adhesive can be prepared in the manner as disclosed in Examples 1–13 of U.S. Pat. No. 5,019,071, the disclosure of which is incorporated by reference above.

Suitable tape components for use in the present invention (for either the attachment strip or the holding strip) include commercially available medical tapes. As previously mentioned, depending on the construction of the article suitable tapes include either double-sided tapes (i.e., tapes coated with adhesive on two major surfaces) or single-sided tapes (i.e., tapes coated with adhesive on one major surface).

Non-limiting examples of acceptable double-sided tape components include No. 1509 transparent polyethylene 0.124 mm double-coated medical tape; No. 1512 transparent polyethylene 0.086 mm double-coated medical tape; No. 1513 transparent polyester 0.086 mm double-coated medical tape; No. 1522 transparent polyethylene 0.160 mm double-coated medical tape; No. 9874 transparent polyethylene 0.122 mm double-coated medical tape; No. 9920 0.024 mm double-coated polyethylene restraint tape; No. 9877 0.114 mm double-coated polyester high performance tape; and No. 9878 water dispersible adhesive tape 0.1 mm double-coated medical tape. All of the above-identified commercially available tapes, (except No. 9877 tape which is a Kraton based medical tape), consist of an appropriate backing coated on both sides with a hypoallergenic, pressure sensitive acrylate adhesive wound with a silicone treated bleached Kraft-Glassine paper liner for adhesive protection. All of the above-identified commercially available tapes are available from Minnesota Mining and Manufacturing Company of St. Paul, Minn., U.S.A. Most of these medical tapes are identified in *3M Medical Specialties Product Reference Guide* published by 3M Health Care in 1991 and available from 3M Medical Specialties Department, the disclosure of which is incorporated by reference herein. The remainder of these medical tapes are also available in publications from 3M Medical Specialties Department. Alternatively, other commercially available tapes are useful. One example is No. 9416 tape commercially available from Minnesota Mining and Manufacturing Company. It is a double coated tape of two different pressure sensitive adhesives having different coating masses flood coated on opposing surfaces of a backing.

Suitable commercially available single-sided medical tapes for use in the present invention include, for example, No. 1523 tan 0.13 mm polyethylene medical tape; No. 1526 transparent 0.13 mm polyethylene medical tape; No. 9830 transparent 0.07 mm polyethylene medical tape; and No. 9835 white 0.14 mm coextruded ethylene vinyl acetate/polyethylene medical tape. Nos. 1523, 1526, and 9830 medical tapes have matte finishes on the non-adhesive surface. Nos. 1523 and 1526 medical tapes have matte finished, non-adhesive surfaces which are corona treated. All of the tapes are coated on one surface with a hypoallergenic, pressure sensitive acrylate adhesive. All of the tapes are wound with a bleached Kraft paper liner (optionally slit lengthwise) having a silicone-treated, polyethylene coated surface. The liner may be separated from the tape during application of the tape to the restraint. All of the enumerated medical tapes are commercially available from Minnesota Mining and Manufacturing Company;

Additional suitable commercially available single-sided medical tapes for use in the present invention include, for example, tapes having nonwoven backings such as No. 1505 heat-sealable 0.16 mm medical tape; No. 1529 microporous rayon nonwoven 0.14 mm medical tape; No. 1776 spunlaced polyester nonwoven 0.29 mm medical tape; No. 9903 microporous nylon nonwoven 0.23 mm medical tape; and No. 9906-W white elastic polyurethane nonwoven 0.23 mm medical tape. All of the enumerated medical tapes are commercially available from Minnesota Mining and Manufacturing Company.

Figure 6:
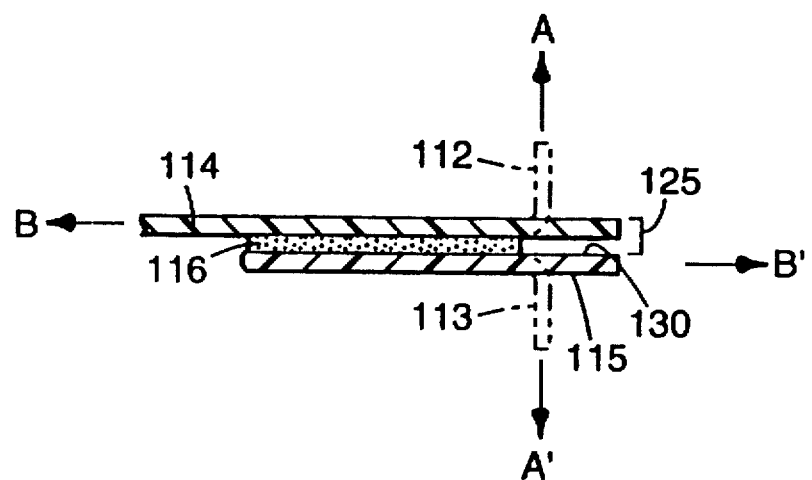
FIG. 6 illustrates the "T-peel" peel force testing mode and the dynamic shear force testing mode.

Peel force in a "T-Peel" direction is used to determine the ease by which the repositionable end of the holding strip of the present invention can be opened by an axial peeling of one end 112 from the other end 113 (as shown in FIG. 6). A "T-Peel" peel force and strength is generated and measured by gripping the ends in an appropriate tensile testing machine (e.g., an INSTRON model 1122 operating at a displacement rate of 30.5 cm/min.) and applying an increasing force as depicted by arrows "A" and "A'." Peel force is measured in Newtons/centimeter width (N/cm). Initial peel force of the holding strip 125 from the upper surface of the attachment strip 130 can range from about 0.09 N/cm to about 2.80 N/cm, desirably from about 0.35 N/cm to about 1.45 N/cm, and preferably from about 0.70 N/cm to about 1.00 N/cm. Such peel force minimizes dexterity required for intended opening of the bridge.

Dynamic shear force is used to measure the strength of the adhesive bond between the holding strip and the attachment strip of each end of the bridge (e.g., the strength of the bond available to resist unintended opening of the bridge by shear forces applied to the bridge strip at an angle other than the axis of the restraint) and between the attachment strip and the surface A dynamic shear force and strength is generated and measured by gripping ends 114 and 115 in an appropriate tensile testing machine (e.g., an INSTRON model 1122 operating at a displacement rate of 30.5 cm/min.) and applying an increasing force as depicted by arrows "B" and "B'." Dynamic shear force is measured in Newtons/centimeter$^2$ (N/cm$^2$). Dynamic shear strength of the bridge forming means can range from about 5 N/cm$^2$ to about 90 N/cm$^2$, desirably from about 10 N/cm$^2$ to about 20 N/cm$^2$, and preferably from about 12 N/cm$^2$ to about 17 N/cm$^2$ in order to assure closure of the bridge.

It is desirable that the tube or cable be easily removed or released from the restraint without need to cut the tube or cable. Preferably, the tube or cable should be easily removed or released from the restraint without the restraint being damaged, i.e., the restraint should be refastenable. By "refastenable," is meant that the tube or cable restraint should easily allow multiple securings and releasings of the tubes and/or cables, even with a gloved hand. This is in contrast to those restraints which only function to secure a cable once (i.e., the release of the cable causes destruction of either the securing means or the cable).

A feature of the restraints of the present invention is the refastenable bridge forming means (i.e., the refastenable adhesive bond between the holding strip and the attachment strip at the repositionable end). The restraints of the present invention preferably allow multiple securings and releasings of the tubes, cables, or objects. This is beneficial in situations where the user desires to add or remove cables from the restraint, or adjust the position of the cable or tube. Most preferably, the tube or cable restraint should be easily used with only one gloved hand. This allows the user to grasp the tubes or cables in one hand yet still operate the restraint.

Most preferably, the restraint comprises a means to facilitate easy opening and closing of the bridge. Suitable means to facilitate easy opening and closing of the bridge include tabs and projections which can be easily grasped by the user to facilitate the peeling open of the repositionable end of the holding strip. Suitable finger tabs for use in the present invention should be of a sufficient size to be easily grasped between the gloved finger and thumb of a typical user, without the glove sticking to the restraint. Preferably, the finger tab is at least 100 mm$^2$, more preferably, the finger tab is at least 400 mm$^2$, most preferably, the finger tab is at least 600 mm$^2$. For ease of manufacture the finger tab preferably comprises a piece of film having a non-adhesive side. The non-adhesive film covers a portion of the adhesive used to repositionably adhere the holding strip to the attachment strip (i.e., near the edge of the restraint). Alternatively, one may "strip coat" an adhesive between the holding strip and the attachment strip in a manner that a portion of the interface between the strips (i.e., near the edge of the restraint) is not covered with adhesive. In addition, where the holding strip comprises a single-sided adhesive tape one may alternatively fold the edge of the holding strip onto itself. This creates a non-adhesive portion which can serve as a finger tab. Finally, one may fabricate the finger tab or a like projection from a separate component and attach the finger tab or projection to the restraint.

Most preferably, the restraint comprises a means to facilitate easy removal of the restraint from the surface to which the restraint is attached. Suitable means to facilitate easy removal of the restraint include tabs and projections which can be easily grasped by the user to facilitate the peeling apart of the restraint from the surface. Most preferably, the removal tab is positioned at the end of the restraint away from the finger tab (i.e., near the fixed end). Suitable removal tabs for use in the present invention should be of a sufficient size to be easily grasped between the finger and thumb of a typical user. Preferably, the removal tab is at least 100 mm$^2$, more preferably the removal tab is at least 400 mm$^2$, most preferably the removal tab is at least 600 mm$^2$.

For ease of manufacture, the removal tab preferably comprises a piece of film having a non-adhesive side. The non-adhesive film covers a portion of the adhesive used to adhere the attachment strip to the surface (i.e., near the edge of the restraint). Alternatively, one may "strip coat" an adhesive on the underside of the attachment strip in a manner that a portion of the attachment strip (i.e., near the edge of the restraint) is not covered with adhesive. In addition, where the attachment strip comprises a single-sided adhesive tape one may alternatively fold the edge of the attachment strip onto itself. This creates a non-adhesive portion which can serve as a removal tab. Similarly, one may fold the edge of the holding strip over onto the bottom side of the attachment strip. This also creates a non-adhesive portion which can serve as a removal tab. Also alternatively, one may slit the liner material which is used to cover the adhesive surface of the attachment strip in such a manner that a portion of the liner (i.e., near the edge of the restraint) can remain covering the adhesive and thus serve as a removal tab.

Preferably, the removal tab is of a rectangular shape and is as wide as the attachment strip. Alternatively, however, the removal tab may have a different shape. For example, one may fold the corner of the attachment strip onto itself (e.g., creating a triangular non-adhesive portion). Likewise, a non-rectangular portion of the liner material or a non-rectangular portion of a non-adhesive film may be utilized as the removal tab.

Preferably, the entire restraint should be capable of being sterilized. Several different sterilization processes are used in the medical field. For example, steam autoclave, gamma radiation, and ethylene oxide may be employed. Preferred restraints should withstand at least one cycle through the desired sterilization process. For example, preferably the restraint should remain functional after irradiation with up to at least 25 kGys gamma cobalt-60 radiation, a dosage often used for sterilization of medical devices. More preferably, the restraint should remain functional after irradiation with up to at least 50 kGys gamma cobalt-60 radiation.

To facilitate the use of a restraint (or help the user determine whether a restraint has been properly used), the restraint may further comprise a visual indicator (e.g., a color indication means). For example, tube and cable restraints of the present invention may comprise multi-colored materials. The use of color may assist the user in a variety of ways. In one embodiment, the "adjustment area" of the tube and cable restraint may be colored in a manner such that when the repositionable end is engaged the colors blend or add together. This helps indicate whether (or to what extent) the bridge forming means is in fact engaged. This indication helps avoid unintentional "misses" between the bridge forming means and the adjustment area. In addition, the finger tab of a restraint may be colored in a distinctive manner (or printed with a distinctive pattern) to direct the users attention to that region.

DETAILED DESCRIPTION OF THE DRAWINGS

Reference is made to the figures wherein like parts have been given like index numbers. Throughout the drawings the various layers of tape, adhesive, or liner material have been exaggerated in thickness for purposes of illustration and clarity. In particular, the adhesive layer is shown in exaggerated thickness. In addition, the size of the various components may be modified, if desired, to accommodate the particular needs of the restraint.

Figure 2A:
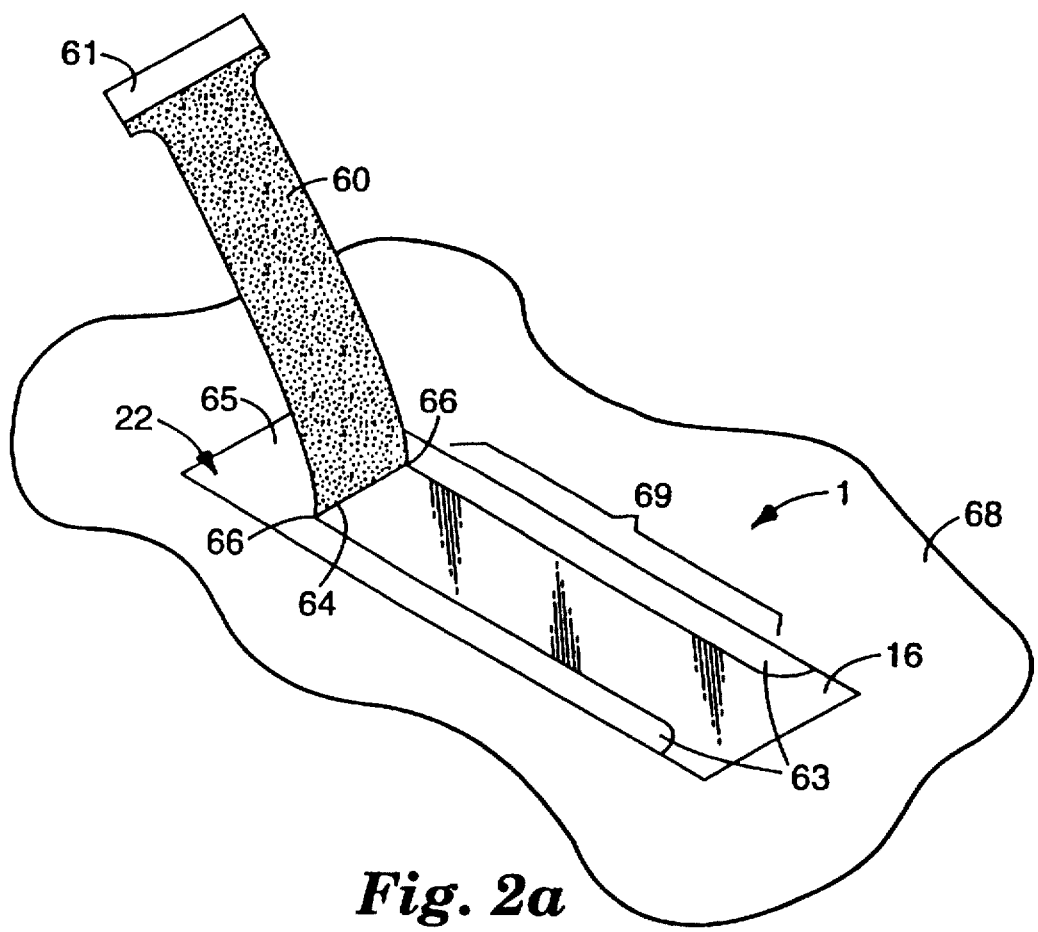
FIGS. 2a and 2b illustrate a tube and cable restraint of the present invention peeled open and restraining a tube or cable, respectively.

FIG. 1a is a cross section of a tube and cable restraint 1 of the present invention having an attachment strip 16 for securing the restraint to a surface and a holding strip 22 for holding a tube or cable. The restraint is shown with a liner material 10 to protect, prior to use, the exposed adhesive of the attachment strip. In addition, a finger tab 13 is shown comprising a tab of material 11 (e.g., adhered to the bottom surface of the holding strip 22). The tab of material 11 provides a non-adhesive interface between the tab 11 and opposing surface of the restraint. The finger tab may be easily grasped between the thumb and finger of the user (even if gloved) and enables the peeling open of the restraint (as shown in FIG. 2a).

Figure 1B:
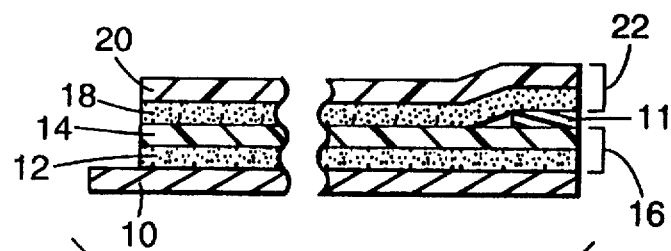
FIGS. 1b and 1c are two enlarged cross section views of each end of the restraints of the present invention where
Figure 1C:
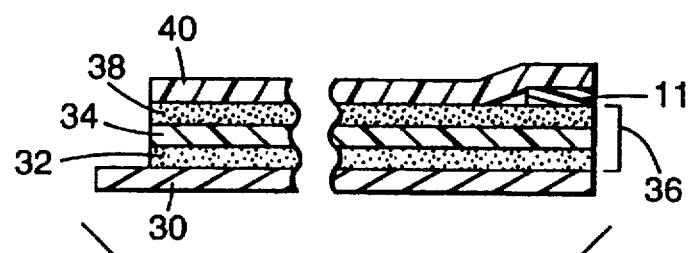

FIGS. 1b and 1c are two enlarged cross section views of the same tube and cable restraint. FIG. 1b illustrates a restraint constructed from two layers of single-sided adhesive tape (16 and 22). In this embodiment, attachment strip 16 comprises a single-sided adhesive tape having adhesive layer 12 and backing material 14; and holding strip 22 comprises a single-sided adhesive tape having adhesive layer 18 and backing material 20. The two tapes may be the same or different in composition. In this embodiment, when the restraint is peeled open adhesive layer 18 remains attached to the underside of backing material 20. Preferably, a low adhesive backsize (not shown) is coated on the top surface of backing 14 to facilitate peel release of adhesive 18. FIG. 1c illustrates a restraint constructed from one layer of a double-sided adhesive tape 36 and a second layer of a non-adhesive film material 40. In this embodiment, attachment strip 36 comprises a double-sided adhesive tape having adhesive layers 32 and 38 and backing layer 34; and holding strip 40 comprises a non-adhesive film. When the restraint is peeled open adhesive layer 38 remains attached to the topside of backing material 34. If desired, a low adhesive backsize (not shown) may be coated on the bottom surface of film 40 to facilitate peel release of adhesive 38. A liner material is shown in both FIGS. 1b and 1c. The liner is removed prior to use to expose the adhesive layer it covers.

Figure 1D:
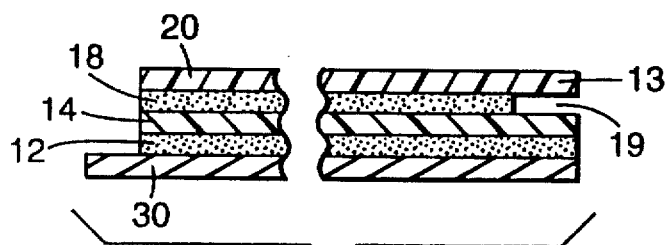
FIGS. 1d and 1e are two enlarged cross section views of the present invention illustrating alternative finger tabs.
Figure 1E:
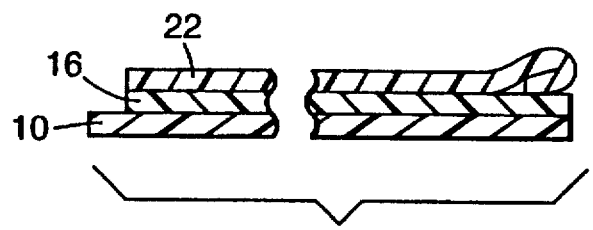

FIGS. 1d and 1e are two alternative enlarged cross section views of the finger tab shown in FIG. 1a. FIG. 1d illustrates a finger tab formed from the holding strip, wherein the bottom surface of the holding strip and the top surface of the attachment strip are free of adhesive along the edge of the restraint and at one end of the restraint (shown at 19). The tab of holding strip may be easily grasped by the user to facilitate peeling open of the restraint. FIG. 1e illustrates a finger tab formed from the holding strip 22 by folding the holding strip over onto itself. In this embodiment the holding strip comprises a single-sided adhesive tape. At one end the tape is folded over onto itself so as to create a tab region where the adhesive is covered.

Figure 1F:
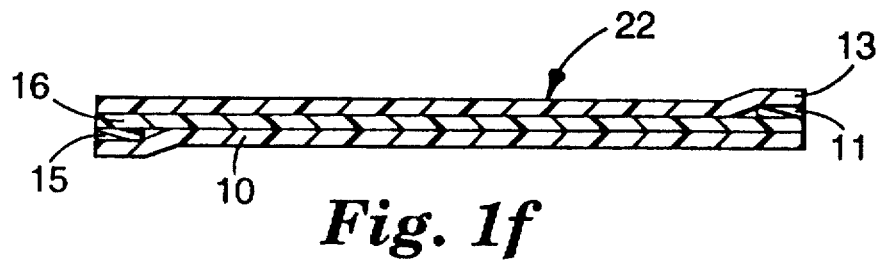
FIGS. 1f, 1g, and 1h are enlarged cross-section views of the present invention illustrating alternative removal tabs which are used to remove the restraint from a surface.
Figure 1G:
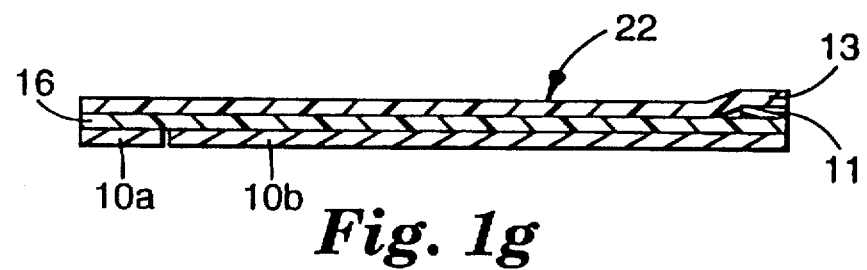
Figure 1H:
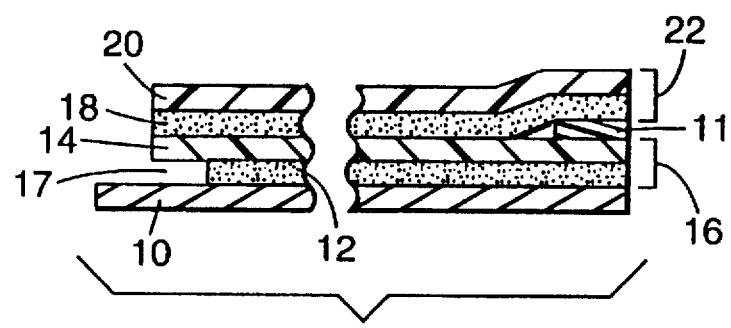

FIGS. 1f, 1g, and 1h are enlarged cross-section views of the present invention illustrating alternative "removal tabs". FIG. If illustrates a removal tab comprising a tab of material 15 (e.g., adhered to the bottom surface of the attachment strip 16). The tab of material 15 provides a non-adhesive interface between the restraint and the surface to which the restraint is attached. The removal tab may be easily grasped between the thumb and finger of the user and enables the easy removal (e.g., by peeling) of the restraint from the surface. FIGS. 1g and 1h are two alternative enlarged cross-section views of the removal tab shown in FIG. 1f. FIG. 1g illustrates a removal tab formed by a portion of liner material 10. In this embodiment, liner 10 is cut into portions 10a and 10b. In use, liner portion 10b is removed and the restraint attached to a surface. Liner portion 10a is left on the restraint and provides a non-adhesive interface between the restraint and the surface. To remove the restraint from the surface one may simply grasp the non-adhered portion of the restraint (i.e., the removal tab) and peel the restraint apart from the surface. FIG. 1h illustrates a removal tab formed from the attachment strip, wherein the bottom surface of the attachment strip is free of adhesive along the edge of the restraint and at one end of the restraint (shown at 17). The tab of adhesive-free attachment strip may be easily grasped by the user to facilitate peeling of the restraint from the surface. Alternatively, (not shown) a removal tab may be formed by folding the attachment strip or holding strip over onto the underside of the attachment strip. This is analogous to the method by which the finger tab of FIG. 1e is formed.

Figure 2B:
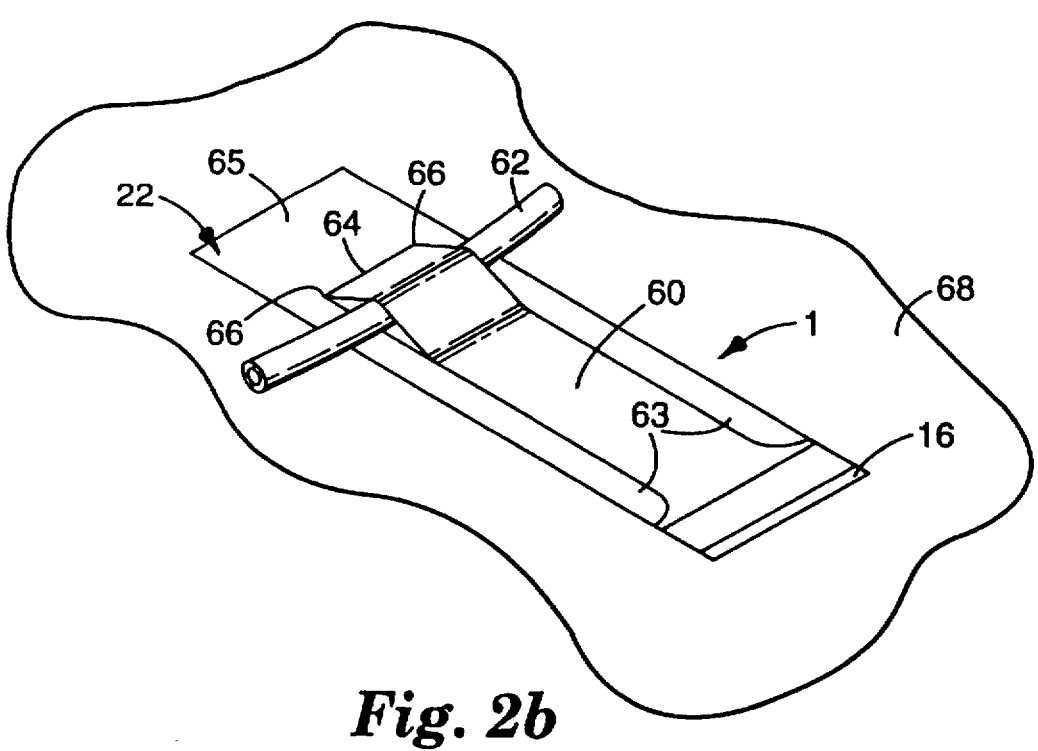

FIGS. 2a and 2b illustrate a tube and cable restraint of the present invention in use holding a tube or cable. Notably, the attachment strip 16 is shown attached to a surface 68 and without any liner material. In addition, the holding strip 22 has been peeled open thus creating a bridging strip 60 which covers the tube 62. The peeling of the holding strip is arrested at the hinge line 64 by the peel stops 66 at the fixed end 65. In use, the attachment strip 16 is first secured to the surface 68 by removing any liner material and contacting the exposed surface of adhesive to the surface. Next, the user peels open the holding strip 22 by grasping the finger tab 61. The peeling is arrested at the hinge line 64 by the peel stops 66 (i.e., by the shear adhesion resistance provided by unpeeled areas 63). A tube or cable 62 is next laid across the restraint at the bridging section 69. The holding strip is then refastened to the attachment strip, as shown in the FIG. 2b, thus containing the tube or cable. The portion of the holding strip that covers the tube or cable is referred to as the bridging strip 60. If desired the tube or cable may be removed or adjusted by repeating this procedure.

Figure 3A:
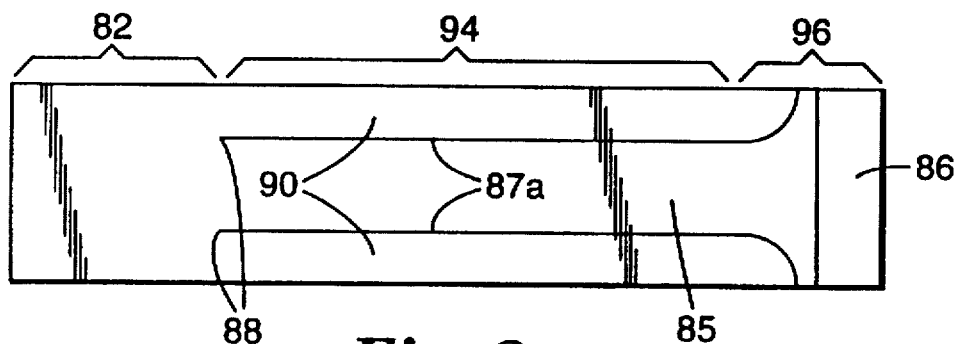
FIGS. 3a, 3b, 3c, 3d, 3e, and 3f are top views of restraints of the present invention illustrating alternative cutting patterns used to create the bridging strip and peel stops.
Figure 3B:
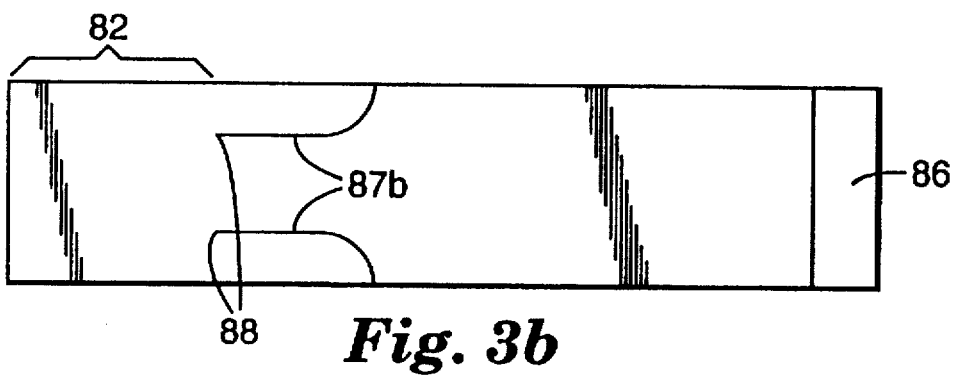
Figure 3C:
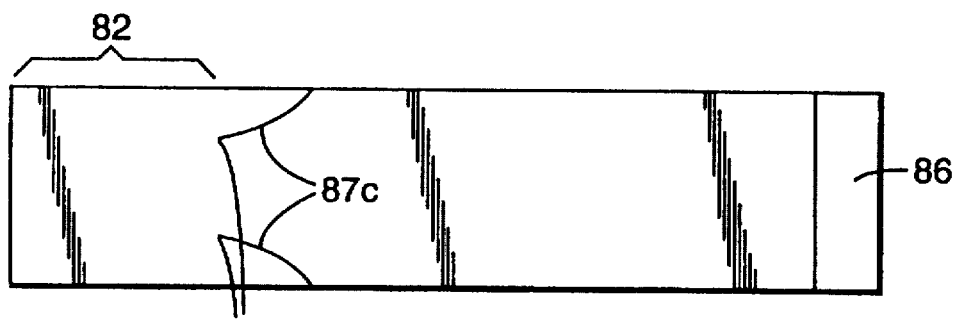
Figure 3D:
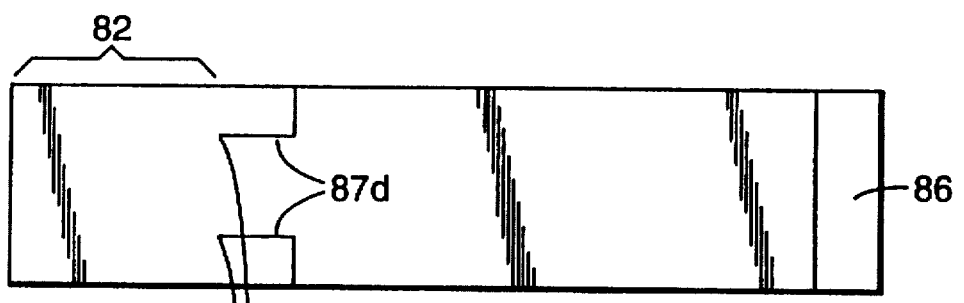
Figure 3E:
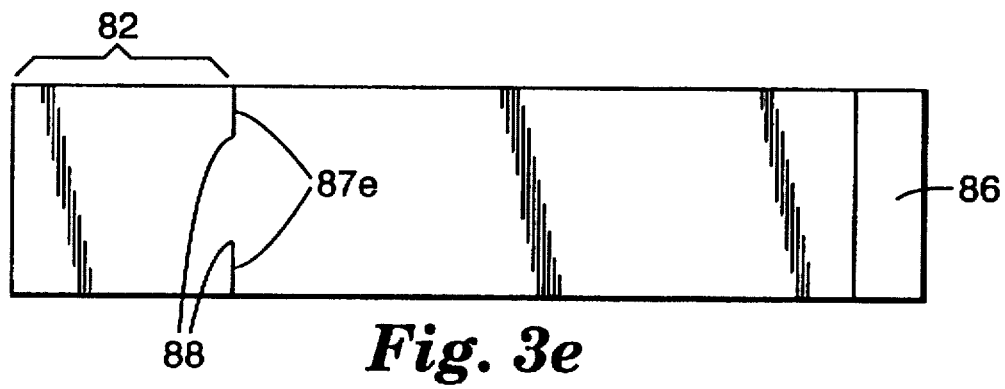
Figure 3F:
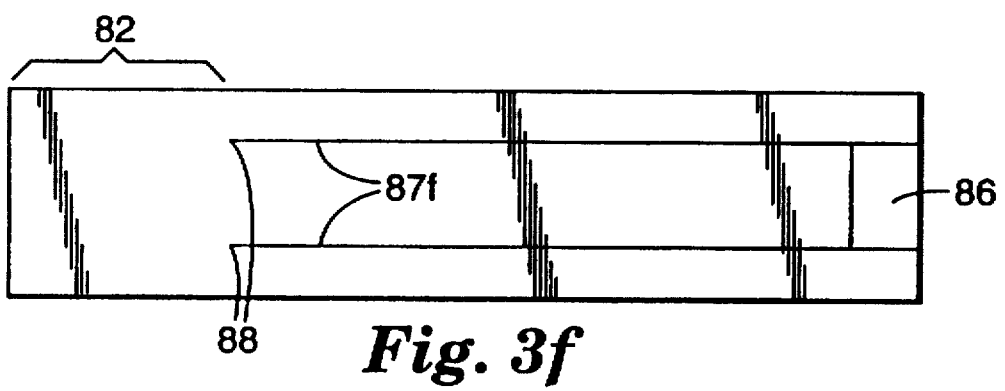

FIGS. 3a, 3b, 3c, 3d, 3e, and 3f are top views of restraints of the present invention illustrating alternative cutting patterns used to create the bridging strip 85 and peel stops 88. FIG. 3a illustrate the presently preferred embodiment of the present invention. The top layer of the restraint is cut (e.g., using a rotary die) creating a portion of the top layer which may be easily peeled apart from the underlying attachment strip. Notably, this peeling is arrested at the fixed end 82. As shown in FIG. 3a the restraint comprises a repositionable end 96 (further comprising a finger tab 86) and a fixed end 82. The repositionable end may be peeled open using the finger tab as a grip and then resealed to secure a tube or cable. When the holding strip is peeled away from the underlying attachment strip it separates along the cut line. That portion of the strip which is connected to the finger tab 86 is peeled away from the attachment strip thus forming the bridging strip 84. That portion which is not peeled away 90 remains attached to the attachment strip. When the holding strip is peeled all the way to the hinge line the attached weed portion acts as peel stops 88 and arrests the peel. This leaves a fixed end 82 which does not separate. If desired, the center of the restraint 94 may optionally be free of adhesive between the bridging strip and the underlying attachment strip. FIGS. 3b, 3c, 3d, 3e, and 3f illustrate similar restraints where the cut pattern (87b, 87c, 87d, 87e, or 87f) is slightly varied. It is contemplated that a variety of patterns may be used to create the peel stops of the present invention. The cut pattern should "interrupt" the peel edge (e.g., by narrowing the peel edge) and create unpeeled areas behind the peel edge which provide shear adhesion, thus arresting the peel. Notably, in FIG. 3e where the cut pattern is near or in-line with the hinge line it is anticipated that plastic deformation of the holding strip near the hinge line will create unpeeled regions behind the hinge line which will arrest the peel. In other words, the hinge line may move a short distance or "bow" due to the plastic deformation of the holding strip thus leaving unpeeled regions which arrest the peel.

Figure 4A:
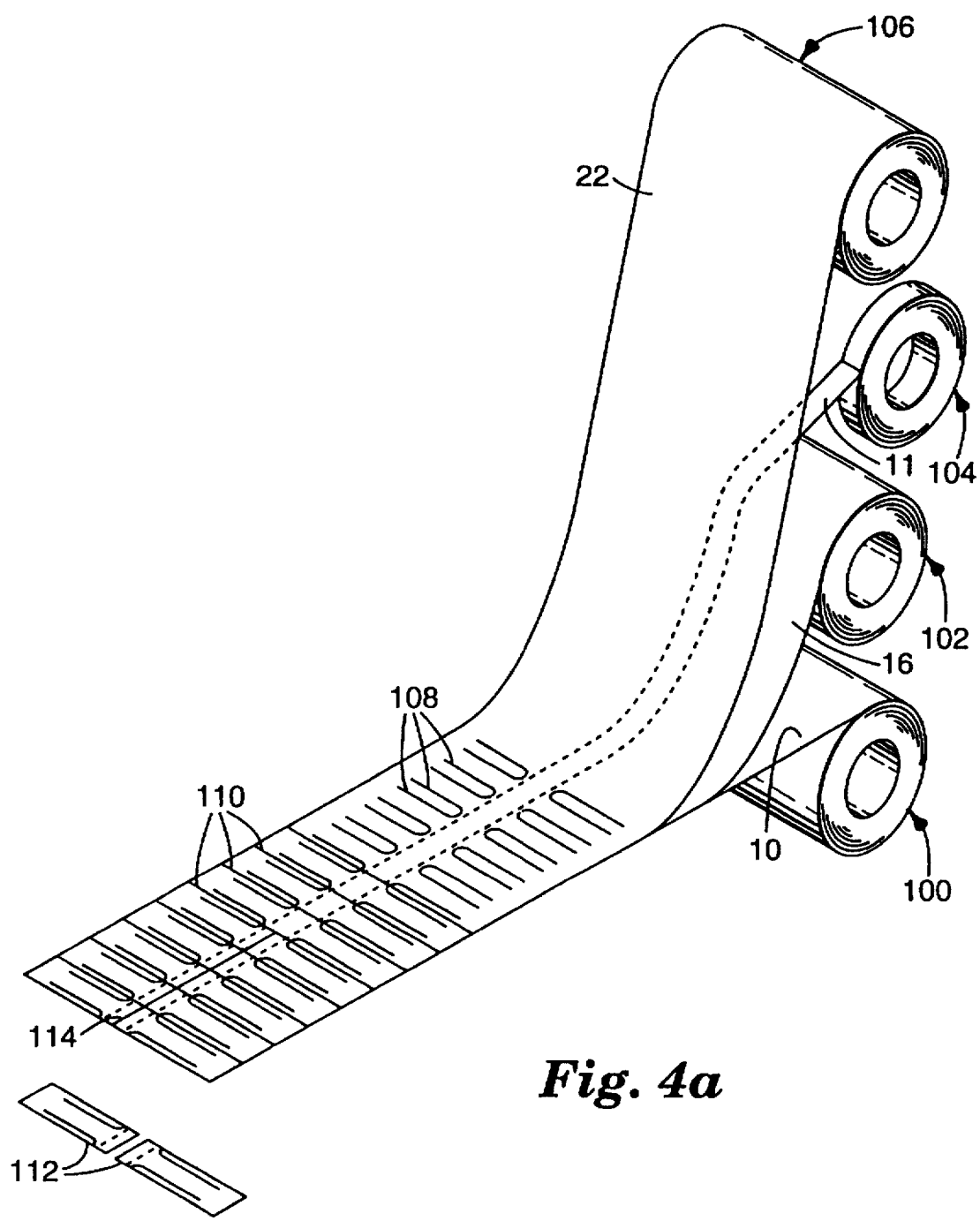
FIGS. 4a and 4b illustrate two methods of making a tube and cable restraint according to the present invention.
Figure 4B:
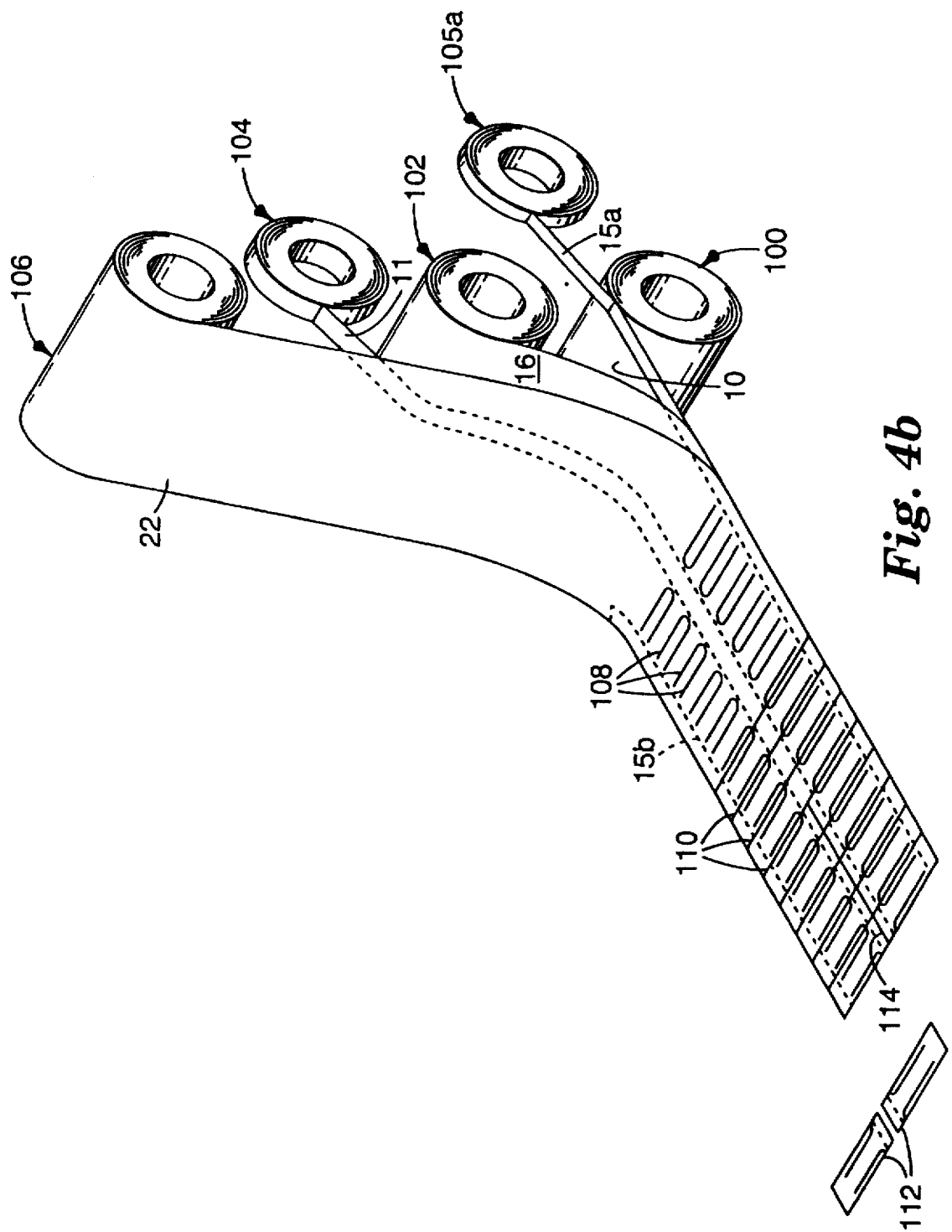

FIGS. 4a and 4b illustrate two presently preferred methods of making the restraints of FIG. 1a and 1f, respectively. Shown in FIG. 4a are four separate rolls ("jumbos") of materials which are first combined, as herein described, and then converted into individual restraints. Roll 100 illustrates a partially unwound large roll of liner material 10. To the surface of the liner material 10 is attached, preferably continuously, a strip of tape 16 from roll 102 (comprising adhesive layer 12 and backing 14). Another roll of tape 22 from roll 106 (comprising adhesive layer 18 and backing 20) is attached to the top surface of tape 16. Between tape 16 and tape 22 is sandwiched a narrow strip of tab material 11 from roll 104. To facilitate attachment of the tapes (to each other, to the tab material and to the liner material) the laminate may be pressed, e.g., between rollers. The laminate is then cut, preferably using a rotary die or dies, and slit. A first pattern used to create the bridging strip 108 severs the laminate to a controlled depth (i.e., severs the top layer of the laminate but doesn't sever the attachment layer or the liner material). Individual restraints are created by cutting across the width of the restraints 110 to a depth that severs the holding strip and the attachment strip. If desired, the liner material may also be cut using this die (thus creating individual restraints 112). Alternatively, one may leave the liner material intact and "peel off" individual restraints from the liner. As shown in FIG. 4a, the laminate is slit along line 114 to separate two adjacent restraints. As shown in FIG. 4b, between tape 16 and liner 10 is sandwiched two narrow strips of removal tab material 15a (from roll 105a) and 15b. Notably, removal tab material 15b is shown using dotted lines and the roll from which it comes is hidden from view.

Figure 5:
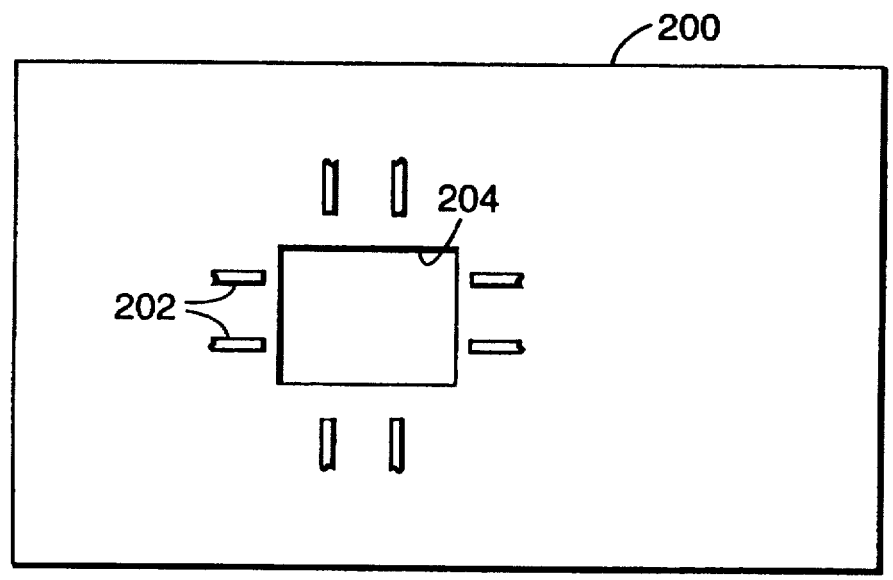
FIG. 5 illustrates a surgical drape of the present invention comprising a plurality of tube and cable restraints attached thereto.

FIG. 5 illustrates a surgical drape 200 of the present invention comprising a plurality of tube and cable restraints 202 attached thereto. The restraints are preferably positioned around an opening 204 through the drape.

FIG. 6 illustrates the "T-peel" peel force testing mode and the dynamic shear force testing mode for a tube and cable restraint of the present invention. It is understood that the principles described in this figure apply to other embodiments of the bridge forming means and is not considered limiting. To generate a T-Peel force (and measure the T-Peel strength) a suitable tensile testing machine is utilized to pull ends 112 and 113 apart as indicated by arrows A and A'. This causes the tapes to peel and separate. Preferably, the bridge forming means 125 (comprising in this embodiment adhesive layer 116 and backing 114) separates between adhesive layer 116 and the adjustment area 130. To generate a dynamic shear force (and measure a dynamic shear strength) a suitable tensile testing machine is utilized to pull ends 114 and 115 as indicated by arrows B and B'.

The following examples are offered to aid in the understanding of the present invention and are not to be construed as limiting the scope thereof. Unless otherwise indicated, all parts and percentages are by weight.

EXAMPLES

Example 1a

Refastenable Tube and Cable Restraint

Several tube and cable restraints were produced as illustrated in FIG. 4a. These restraints comprise two different layers of single-sided tape (shown as 16 and 22), a non-adhesive film tab piece (shown as 11), and a removable liner (shown as 10).

A layer of No. 1516 clear polyester single-sided adhesive tape (measuring 30 cm wide and available from 3M Company, St. Paul Minn.) was placed atop the center of a liner material measuring 32 cm wide. A narrow strip of blue polyethylene was placed atop the center of the 1516 tape and held in place with a layer of No. 9833 white polyethylene single-sided adhesive tape (measuring 30 cm wide and available from 3M Company, St. Paul Minn.).

The above laminate was die cut as illustrated in FIG. 3a using a rotary die to form a bridging strip and peel stops. This first die cut severed only the top tape layer of the laminate. A second rotary die was used to sever the laminate across the web thereby separating individual restraints. The web was also slit in half to produce two mirror image narrower webs of restraints. The slitting operation cut through the two tape layers, the tab film and the liner material. Individual restraints measured 15.5 cm long by 3.81 cm wide. The finger tab measured 3.81 cm by 1 cm. An extra 1 cm of liner was exposed on one end of the restraint to facilitate peeling apart the liner from the attachment tape.

In use, the tube and cable restraint adheres well to skin and surgical drape and gown fabrics. The holding strip can be easily peeled apart from the underlying attachment strip yet the peel is effectively arrested 3 cm from the end of the restraint by the peel stops. The tube and cable restraint effectively secures a tube or cable to the surface without unintended detachment.

Example 1b

Refastenable Tube and Cable Restraint

Several tube and cable restraints are produced as illustrated in FIG. 4b. These restraints comprise two different layers of single-sided tape (shown as 16 and 22), two non-adhesive film tab pieces (shown as 11 and 15), and a removable liner (shown as 10).

A layer of No. 1516 clear polyester single-sided adhesive tape (measuring 30 cm wide and available from 3M Company, St. Paul Minn.) is placed atop the center of a liner material measuring 32 cm wide. Two narrow strips of polyethylene are sandwiched between the top of the liner material and the bottom of the 1516 tape material along each edge of the tape material. A narrow strip of blue polyethylene is placed atop the center of the 1516 tape and held in place with a layer of No. 9833 white polyethylene single-sided adhesive tape (measuring 30 cm wide and available from 3M Company, St. Paul Minn.).

The above laminate is die cut as illustrated in FIG. 3a using a rotary die to form a bridging strip and peel stops. This first die cut severed only the top tape layer of the laminate. A second rotary die is used to sever the laminate across the web thereby separating individual restraints. The web is also slit in half to produce two mirror image narrower webs of restraints. The slitting operation cuts through the two tape layers, the tab film and the liner material. Individual restraints measure 15.5 cm long by 3.81 cm wide. The finger tab and the removal tab each measure 3.81 cm by 1 cm.

In use, the tube and cable restraint adheres well to skin and surgical drape and gown fabrics. The holding strip can be easily peeled apart from the underlying attachment strip yet the peel is effectively arrested 3 cm from the end of the restraint by the peel stops. The tube and cable restraint effectively secures a tube or cable to the surface without unintended detachment. The tube and cable restraint may be easily removed from the surface to which it is adhered by grasping the removal tab and peeling the restraint away from the surface. A restraint with a removal tab is easier to grasp and remove from the surface than a restraint without a removal tab.

Example 2

Peel and Dynamic Shear Strength

To test the restraints for peel strength and dynamic shear strength the following operations were performed. A 2 kg rubber coated roller was used to press closed the holding strip (in this case a strip of No. 1516 clear polyester single-sided adhesive tape available from 3M Company, St. Paul Minn.) to the top surface of the attachment strip (in this case a strip of No. 9833 white polyethylene single-sided adhesive tape available from 3M Company, St. Paul Minn.). Peel adhesion force of the holding strip was measured on an Instron 1122 tensile tester using the "T-Peel" test as illustrated in FIG. 6. The displacement rate of the tensile tester was 30.5 cm/min. Force was measured in grams per 3.81 cm width and converted to N/cm width. The mean value of peel strength was about 0.36 N/cm width.

Dynamic shear force was similarly measured on an Instron 1122 tensile tester operating at a displacement rate of 30.5 cm/min. The area of adhesive contact between the holding strip and attachment strip was 3.81 cm wide by 5.08 cm long (19.35 cm$^2$). The mean shear force applied to failure was about 57.8 N. This translates to a dynamic shear strength of about 2.986 N/cm$^2$. Notably, the holding strip began to neck down during this test, causing peeling to occur. It is anticipated that the shear strength would be considerably higher if this peeling were restrained.

The tensile strength of the holding strip was measured by gripping the ends of the tape in an INSTRON tensile tester operating at 30.5 cm/min. Notably, the ends of the tape were first sandwiched between two pieces of tabbing tape in such a way as to leave only the specified gauge length exposed and to leave the ends of the tape tabs outside the jaw faces. For a 2.54 cm wide sample and a 15 cm gauge length the tensile strength was calculated to be 12.25 N/cm width. This results demonstrate that refastenable tube and cable restraints of the present invention peel open easily yet have exceptional dynamic shear strength and tensile strength.

Various modifications and alterations of this invention will be apparent to those skilled in the art without departing from the scope and spirit of this invention, and it should be understood that this invention is not limited to the illustrative embodiments set forth herein.

What is claimed is:

1. A tube restraint, comprising:
   an attachment strip of flexible material having on its underside a coating of adhesive suitable for adhering to a surface;
   a holding strip of flexible material having a fixed end, a repositionable end and a bridging strip there between, wherein said holding strip is die cut through its top surface in a manner so as to retard peel at the fixed end by providing integral peel stops comprising unpeeled regions of the holding strip behind a hinge line of the tube restraint at the fixed end, wherein the bridging strip is narrower than the holding strip at the fixed end; and
   an adhesive layer between the bottom surface of said holding strip and the top surface of said attachment strip at least near each end of said restraint.

2. A tube restraint according to claim 1, wherein said attachment strip and said holding strip comprise materials selected from the group consisting of cloth, nonwoven fabrics, foams, plastic materials and laminates of these materials.

3. A tube restraint according to claim 1, wherein said attachment strip and said holding strip each independently comprise a plastic sheet materials selected from the group consisting of polyester and polyethylene and wherein said bridging strip has a tensile strength of at least 5 N/cm width.

4. A tube restraint according to claim 3, wherein said plastic sheet materials have a thickness at least 0.07 mm, and wherein said coating of adhesive and adhesive layer are water dispersible.

5. A tube restraint according to claim 1, wherein said bridging strip is at least 10 cm in length and at least 2 cm wide.

6. A tube restraint according to claim 1, wherein said attachment strip comprises a single-sided pressure sensitive adhesive tape, and said holding strip comprises a single-sided pressure sensitive adhesive tape.

7. A tube restraint according to claim 1, wherein said attachment strip comprises a double-sided pressure sensitive adhesive tape, and said holding strip comprises a non-adhesive plastic sheet material.

8. A tube restraint according to claim 1, wherein said holding strip is die cut in a manner to provide integral peel stops comprising unpeeled regions of said holding strip behind the hinge line of said restraint at the fixed end.

9. A tube restraint according to claim 8, wherein said bridging strip is narrower than said holding strip at the fixed end.

10. A tube restraint according to claim 9, wherein said restraint is at least 14 cm long and at least 2 cm wide.

11. A tube restraint according to claim 8, further comprising a liner material attached to said adhesive coating on the underside of said attachment strip of flexible material.

12. A tube restraint according to claim 8, wherein said restraint is attached to a surgical drape or gown.

13. A tube restraint according to claim 1, wherein said surface is selected from the group consisting of a surgical drape, gown, and skin.

14. A tube restraint according to claim 1, further comprising a finger tab at the edge of said restraint at the repositionable end.

15. A tube restraint according to claim 14, wherein said finger tab is at least 600 mm$^2$ and comprises a piece of non-adhesive film adhered to said adhesive layer between the bottom surface of said holding strip and the top surface of said attachment strip.

16. A tube restraint according to claim 1, wherein said restraint further comprises a removal tab at the edge of said restraint at the fixed end to facilitate easy removal of said restraint from said surface.

17. A tube restraint, comprising:
   an attachment strip of flexible material having on its underside a coating of adhesive suitable for adhering to a surface, wherein said attachment strip comprises a single-sided pressure sensitive adhesive tape;
   a holding strip of flexible material having a fixed end, a repositionable end and a bridging strip there between, wherein said holding strip comprises a single-sided pressure sensitive adhesive tape, and wherein said holding strip is cut through its top surface in a manner to provide integral peel stops comprising unpeeled regions of said holding strip behind the hinge line of said restraint at the fixed end;
   an adhesive layer between the bottom surface of said holding strip and the top surface of said attachment strip at least near each end of said restraint; and
   a finger tab at the edge of said restraint at the repositionable end.

18. A tube restraint, comprising:
   an attachment strip of a flexible plastic sheet material having on its underside a coating of adhesive suitable for adhering to a surface;
   a holding strip of a flexible plastic sheet material having a fixed end, a repositionable end and a bridging strip there between, wherein said holding strip is cut through its top surface in a manner so as to retard peel at the fixed end, and wherein said bridging strip has a tensile strength of at least 5 N/cm width;
   an adhesive layer between the bottom surface of said holding strip and the top surface of said attachment strip at least near each end of said restraint;

a finger tab at the edge of said restraint at the repositionable end; and a liner material attached to said adhesive coating on the underside of said attachment strip of flexible material.

19. A tube restraint, comprising:

an attachment strip of flexible material having on its underside a coating of adhesive suitable for adhering to a surface;

a holding strip of flexible material having a fixed end, a repositionable end and a bridging strip there between, wherein the holding strip is cut through its top surface in a manner so as to retard peel at the fixed end; and an adhesive layer between the bottom surface of the holding strip and the top surface of the attachment strip at least near each end of the restraint, wherein said restraint is substantially free of adhesive on the surfaces between said fixed end and said repositionable end that are adapted to form a bridge about said tube.

* * * * *